US011039615B2

(12) United States Patent
McGuire, Jr.

(10) Patent No.: US 11,039,615 B2
(45) Date of Patent: Jun. 22, 2021

(54) METHODS OF PROCESSING CHLORHEXIDINE-CONTAINING POLYMERIZABLE COMPOSITIONS AND ANTIMICROBIAL ARTICLES FORMED THEREBY

(71) Applicant: entrotech life sciences, inc., San Francisco, CA (US)

(72) Inventor: James E. McGuire, Jr., Palm Beach, FL (US)

(73) Assignee: entrotech life sciences, inc., San Francisco, CA (US)

( * ) Notice: Subject to any disclaimer, the term of this patent is extended or adjusted under 35 U.S.C. 154(b) by 259 days.

(21) Appl. No.: 14/888,673

(22) PCT Filed: Apr. 17, 2015

(86) PCT No.: PCT/US2015/026547
§ 371 (c)(1),
(2) Date: Nov. 2, 2015

(87) PCT Pub. No.: WO2015/161302
PCT Pub. Date: Oct. 22, 2015

(65) Prior Publication Data
US 2016/0050934 A1    Feb. 25, 2016

Related U.S. Application Data

(60) Provisional application No. 61/981,710, filed on Apr. 18, 2014.

(51) Int. Cl.
| | |
|---|---|
| *A01N 47/44* | (2006.01) |
| *A01N 25/10* | (2006.01) |
| *A61L 15/46* | (2006.01) |
| *A61L 15/58* | (2006.01) |
| *A61K 9/70* | (2006.01) |
| *A61K 31/155* | (2006.01) |

(52) U.S. Cl.
CPC ............ *A01N 47/44* (2013.01); *A01N 25/10* (2013.01); *A61K 9/7061* (2013.01); *A61K 9/7069* (2013.01); *A61K 31/155* (2013.01); *A61L 15/46* (2013.01); *A61L 15/58* (2013.01); *A61L 2300/206* (2013.01); *A61L 2300/404* (2013.01)

(58) Field of Classification Search
CPC .............................. A61K 9/7069; A01N 47/44
See application file for complete search history.

(56) References Cited

U.S. PATENT DOCUMENTS

| | | |
|---|---|---|
| 2,684,924 A | 7/1954 | Rose et al. |
| 2,804,073 A | 8/1957 | Gallienne et al. |
| 2,884,126 A | 4/1959 | Ulrich |
| 3,577,516 A | 5/1971 | Gould et al. |
| 3,608,070 A | 9/1971 | Nouvel |
| 3,932,607 A | 1/1976 | Hesselgren |
| 3,975,350 A | 8/1976 | Hudgin et al. |
| 4,181,752 A | 1/1980 | Martens et al. |
| 4,310,509 A | 1/1982 | Berglund et al. |
| 4,323,557 A | 4/1982 | Rosso et al. |
| 4,476,293 A | 10/1984 | Robinson |
| 4,499,896 A | 2/1985 | Heinecke |
| 4,563,388 A | 1/1986 | Bonk et al. |
| 4,584,192 A | 4/1986 | Dell et al. |
| 4,643,180 A | 2/1987 | Feld et al. |
| 4,666,896 A | 5/1987 | Warner et al. |
| 4,798,201 A | 1/1989 | Rawlings et al. |
| 4,999,210 A | 3/1991 | Solomon et al. |
| 5,013,306 A | 5/1991 | Solomon et al. |
| 5,015,228 A | 5/1991 | Columbus et al. |
| 5,017,625 A | 5/1991 | Ansell |
| 5,045,601 A | 9/1991 | Capelli et al. |
| 5,069,907 A | 12/1991 | Mixon et al. |
| 5,089,205 A | 2/1992 | Huang et al. |
| 5,165,952 A | 11/1992 | Solomon et al. |
| 5,183,664 A | 2/1993 | Ansell |
| 5,225,473 A | 7/1993 | Duan |
| 5,290,615 A | 3/1994 | Tushaus et al. |
| 5,369,155 A | 11/1994 | Asmus |

(Continued)

FOREIGN PATENT DOCUMENTS

| | | |
|---|---|---|
| CN | 101322661 | 12/2008 |
| EP | 0196459 | 10/1986 |

(Continued)

OTHER PUBLICATIONS

Room Temperature: retrieved from internet: http://www.merriam-webster.com/dictionary/room%20temperature. Retrieved on Oct. 3, 2016.*
Premjeet et al.: Transdermal Drug Delivery System (Patches), Applications in Present Scenario: retrieved from internet: http://www.ijrpc.com/files/1194-49.pdf. Retrieved on Oct. 3, 2016.*
Chlorhexidine digluconate: retrieved from internet: http://corporate.evonik.com/_layouts/Websites/Internet/DownloadCenterFileHandler.ashx?fileid=1115. Retrieved on Mar. 27, 2017.*
Prepolymer: retreived form internet: https://www.merriam-webster.com/dictionary/prepolymer. Retrieved on Mar. 27, 2017.*

(Continued)

*Primary Examiner* — Hong Yu
(74) *Attorney, Agent, or Firm* — The Griffith Law Firm, A P.C.; Lisa M. Griffith

(57) ABSTRACT

Advantageously, para-chloroaniline (PCA) is minimal in antimicrobial articles prepared according to the method of the invention. A method of forming an antimicrobial article according to the invention comprises steps of: providing a polymerizable composition; incorporating an antimicrobially effective amount of at least one chlorhexidine-containing antimicrobial agent into the polymerizable composition; and, polymerizing the polymerizable composition to form chlorhexidine-containing polymer of the antimicrobial article, wherein processing temperature during the method is less than about 80° C.

21 Claims, No Drawings

(56) References Cited

U.S. PATENT DOCUMENTS

| | | | |
|---|---|---|---|
| 5,382,451 A | 1/1995 | Johnson et al. |
| 5,389,093 A | 2/1995 | Howell |
| 5,616,338 A | 4/1997 | Fox et al. |
| 5,645,855 A | 7/1997 | Lorenz |
| 5,686,096 A | 11/1997 | Khan et al. |
| 5,690,958 A | 11/1997 | McGrath |
| 5,707,366 A | 1/1998 | Solomon et al. |
| 5,717,005 A | 2/1998 | Richardson |
| 5,763,412 A | 6/1998 | Khan et al. |
| 5,803,086 A | 9/1998 | Scholz et al. |
| 5,985,395 A | 11/1999 | Comstock et al. |
| 6,102,205 A | 8/2000 | Greff et al. |
| 6,106,505 A | 8/2000 | Modak et al. |
| 6,132,765 A | 10/2000 | DiCosmo et al. |
| 6,139,856 A | 10/2000 | Kaminska et al. |
| 6,224,579 B1 | 5/2001 | Modak et al. |
| 6,228,393 B1 | 5/2001 | DiCosmo et al. |
| 6,461,467 B2 | 10/2002 | Blatchford et al. |
| 6,475,516 B2 | 11/2002 | DiCosmo et al. |
| 6,488,948 B1 | 12/2002 | Danieli |
| 6,500,466 B2 | 12/2002 | Werle et al. |
| 6,579,539 B2 | 6/2003 | Lawson et al. |
| 6,582,719 B2 | 6/2003 | Modak et al. |
| 6,596,401 B1 | 7/2003 | Terry et al. |
| 6,607,746 B2 | 8/2003 | Cox et al. |
| 6,742,522 B1 | 6/2004 | Baker et al. |
| 6,808,738 B2 | 10/2004 | DiTizio et al. |
| 6,838,078 B2 | 1/2005 | Wang et al. |
| 6,843,784 B2 | 1/2005 | Modak et al. |
| 6,872,195 B2 | 3/2005 | Modak et al. |
| 6,939,554 B2 | 9/2005 | McDonald et al. |
| 7,066,916 B2 | 6/2006 | Keaty et al. |
| 7,189,793 B2 | 3/2007 | Wang et al. |
| 7,297,143 B2 | 11/2007 | Woloszko et al. |
| 7,323,163 B2 | 1/2008 | Wang et al. |
| 7,329,412 B2 | 2/2008 | Modak et al. |
| 7,427,574 B2 | 9/2008 | Allen |
| 7,488,757 B2 | 2/2009 | Hoang |
| 7,537,779 B2 | 5/2009 | Modak et al. |
| 7,771,743 B1 | 8/2010 | Luthra et al. |
| 7,999,023 B2 | 8/2011 | Menon et al. |
| 8,026,407 B2 | 9/2011 | Downs et al. |
| 8,354,123 B2 | 1/2013 | DiTizio et al. |
| 8,361,501 B2 | 1/2013 | DiTizio et al. |
| 8,383,143 B2 | 2/2013 | Modak et al. |
| 8,481,138 B2 | 7/2013 | Miller et al. |
| 8,591,493 B2 | 11/2013 | McGuire |
| 9,028,852 B2 | 5/2015 | Scholz |
| 2001/0055511 A1 | 12/2001 | Baumann et al. |
| 2002/0051812 A1 | 5/2002 | DiCosmo et al. |
| 2003/0224033 A1 | 12/2003 | Li et al. |
| 2004/0086568 A1 | 5/2004 | DiTizio et al. |
| 2004/0126355 A1 | 7/2004 | Childers |
| 2004/0137065 A1 | 7/2004 | Vogt et al. |
| 2005/0137375 A1* | 6/2005 | Hansen ............ C08G 18/0823 528/44 |
| 2005/0158252 A1 | 7/2005 | Romanowski et al. |
| 2007/0009580 A1 | 1/2007 | DiCosmo et al. |
| 2007/0212419 A1* | 9/2007 | Bako ............ A61K 9/0024 424/487 |
| 2008/0026015 A1 | 1/2008 | MacDonald et al. |
| 2008/0026025 A1 | 1/2008 | Gooch et al. |
| 2008/0060550 A1 | 3/2008 | MacDonald et al. |
| 2008/0063615 A1 | 3/2008 | MacDonald et al. |
| 2008/0078413 A1 | 4/2008 | Padget et al. |
| 2008/0142023 A1 | 6/2008 | Schmid et al. |
| 2009/0035388 A1 | 2/2009 | Dudnyk et al. |
| 2009/0098073 A1 | 4/2009 | MacDonald et al. |
| 2009/0098081 A1 | 4/2009 | MacDonald et al. |
| 2009/0123569 A1 | 5/2009 | MacDonald et al. |
| 2009/0155197 A1 | 6/2009 | Smith et al. |
| 2010/0022654 A1 | 1/2010 | Asmus et al. |
| 2010/0069854 A1 | 3/2010 | Okoh et al. |
| 2010/0087788 A1 | 4/2010 | Rosenblatt et al. |
| 2010/0234815 A1 | 9/2010 | Do et al. |
| 2010/0282409 A1 | 11/2010 | Hobbs et al. |
| 2011/0100293 A1 | 5/2011 | Abbasian et al. |
| 2011/0100294 A1 | 5/2011 | Abbasian et al. |
| 2011/0104390 A1 | 5/2011 | Abbasian et al. |
| 2011/0137006 A1 | 6/2011 | McGuire, Jr. et al. |
| 2011/0152925 A1 | 6/2011 | Schorr et al. |
| 2011/0212152 A1 | 9/2011 | DiTizio et al. |
| 2011/0241261 A1 | 10/2011 | McGuire, Jr. et al. |
| 2011/0256185 A1 | 10/2011 | Yang et al. |
| 2011/0290259 A1 | 12/2011 | McGuire, Jr. et al. |
| 2011/0313048 A1 | 12/2011 | Yang et al. |
| 2012/0330210 A1 | 12/2012 | Yang et al. |
| 2013/0039953 A1 | 2/2013 | Dudnyk et al. |
| 2013/0065965 A1 | 3/2013 | Salguero et al. |
| 2013/0239977 A1 | 9/2013 | McGuire, Jr. |
| 2013/0303656 A1 | 11/2013 | Wibaux et al. |
| 2015/0165097 A1 | 6/2015 | Parthasarathy et al. |
| 2015/0238444 A1 | 8/2015 | Menon et al. |
| 2015/0322229 A1 | 11/2015 | Bui et al. |
| 2015/0328360 A1 | 11/2015 | Menon et al. |
| 2016/0001058 A1 | 1/2016 | Ziebol et al. |
| 2016/0081894 A1 | 3/2016 | Hoang et al. |
| 2016/0296678 A1 | 10/2016 | Menon et al. |

FOREIGN PATENT DOCUMENTS

| | | |
|---|---|---|
| EP | 0379269 | 3/1994 |
| EP | 2229964 | 9/2010 |
| EP | 2229964 A1 | 9/2010 |
| EP | 2373270 | 10/2011 |
| GB | 2349644 A | 11/2000 |
| WO | WO-90/00066 | 1/1990 |
| WO | WO-93/02717 | 2/1993 |
| WO | WO-98/51352 | 11/1998 |
| WO | WO-00/57933 | 10/2000 |
| WO | WO-02/051464 | 7/2002 |
| WO | WO-03/066721 A1 | 8/2003 |
| WO | WO-2007/132239 | 11/2007 |
| WO | WO-2009/015476 | 2/2009 |
| WO | WO-2010/080936 | 7/2010 |
| WO | WO-2011/061272 | 5/2011 |
| WO | WO-2011/061272 A1 | 5/2011 |
| WO | WO-2011/156910 | 12/2011 |
| WO | WO-2012/100244 | 7/2012 |
| WO | WO-2013/142537 | 9/2013 |
| WO | WO-2014/124232 | 8/2014 |
| WO | WO-2015/161302 | 10/2015 |

OTHER PUBLICATIONS

Monomers, Oligomers, Polymers, and Macromolecules (Overview): retrieved from internet: https://link.springer.com/content/pdf/10.1007%2F978-3-642-36199-9_237-1.pdf. Retrieved on Mar. 13, 2018.*

Polymer Properties Database: retrieved from internet: http://polymerdatabase.com/Adhesives/Urethane%20Adhesives.html. Retrieved on Mar. 13, 2018.*

Oligomerize: retrieved from internet: https://en.oxforddictionaries.com/definition/oligomerize. Retrieved on Mar. 13, 2018.*

Kinetic study of the polymerization of aromatic polyurethane prepolymers by high-throughput experimentation: https://onlinelibrary.wiley.com/doi/full/10.1002/pola.23768. retrieved on May 2, 2018.*

Introduction to Polyurethane Chemistry and Structure-Property Relationships: http://www.pmahome.org/files/5514/6263/3426/01_IntroductiontoPolyurethane.pdf. retrieved on May 2, 2018.*

Polyacrylates: http://pslc.ws/macrog/acrylate.htm. retrieved on May 3, 2018.*

"3M DuraPrep Surgical Solution—Patient Preoperative Skin Preparation," *Technical Brochure*, 3M Company (St. Paul, MN) (Sep. 29, 2006).

"3M DuraPrep Surgical Solution (Iodine Povacrylex [0.7% available Iodine] and Isopropyl Alcohol, 74% w/w) Patient Preoperative Skin Preparation," http://solutions.3m.com/wps/portal/3M/en_US/infection-prevention-solutions/home/products/?PC_7_RJH9U52308DUB0IIL8TMGN3013000000_nid=GSF83Z3YYXbeFM2XGMRS15gl.

(56) References Cited

OTHER PUBLICATIONS

"3M DuraPrep Surgical Solution Drug Label," http://dailymed.nlm.nih.gov/dailymed/drugInfo.cfm?id=38755.
"3M Incise Drapes," *3M Technical Brochure*, 3M Company (St. Paul, MN) (Jan. 1, 2001).
"3M Incise Drapes: Bibliography of Efficacy and Safety Studies," *3M Technical Brochure*, 3M Company (St. Paul, MN) (Jan. 1, 2002).
"3M Tegaderm CHG Chlorhexidine Gluconate IV Securement Dressing," *3M Technical Brochure*, 3M Company (St. Paul, MN) (Jan. 1, 2007).
"Antimicrobial Susceptibility Test: Zone of Inhibition," *Doc. No. STP0124*, Nelson Laboratories, Inc. (Salt Lake City, UT) (Jan. 1, 2006).
"Cesarean/Abdominal Fluid Collection Drape With Fenestration, 100 in.×72 in.×120 in., Sterile," http://nacrm.kcmkt.com/scripts/wgate/zkcnab2c/!?p_shop=ZKCHCSHOP, (Jan. 9, 2009).
"ChloraPrep 26mL Applicator," CareFusion Corporation (2011).
"Chloraprep One-Step—chlorhexidine gluconate and isopropyl alcohol solution—Drug Label," http://nccs-dailymed.nlm.nih.gov/dailymed/archives/fdaDrugInfo.cfm?archiveid=11471 (Nov. 9, 2011).
"Dow Aculyn 22," (Sep. 2002) pp. 1-12.
"Dow Corning Soft Skin Adhesives Parts A & B," *Dow Corning Product Information*, Ref. No. 52-1128-01 (Jul. 31, 2009).
"MCD—Disposable Surgical Drapes Cross Reference," http://www.medconceptsdev.com/products_D_Xreference.htm, (Jan. 9, 2009).
"MCD—Surgical Drapes," http://www.medconceptsdev.com/Catalog_template.asp?top=acti-gard&cid=99, (Jan. 9, 2009).
"SurgiClear Antimicrobial Clear Silicone Adhesive Dressing with Chlorhexidine and Silver," www.covalon.com; Covalon Technologies Ltd.
"The Power of Povacrylex," 3M Company (Dec. 31, 2009).
"Topical Antimicrobials in the Control of Wound Bioburden—Part 2," *Ostomy Wound Management*, vol. 52, Issue 8 (Aug. 2006) pp. 1-10.
Basrani, Bettina R., et al., "Using Diazotization to Characterize the Effect of Heat or Sodium Hypochlorite on 2.0% Chlorhexidine," *Jour. of Endodont.*, vol. 35, No. 9 (Sep. 2009) pp. 1296-1299.
Boehncke, A. et al., "4-Chloroaniline," *Concise International Chemical Assessment Document 48*, World Health Organization, ISBN 92 4 153048 0 (2003).
Cropper, E. et al., "Analytical Procedures for the Determination of Chlorhexidine in Oral Products," *J. Soc. Cosmet.*, vol. 26 (1975) pp. 355-373.
Decker, C., "The Use of UV Irradiation in Polymerization," *Polym. Int.*, 45:133-141 (Mar. 26, 1999).
Ditizio, Val et al., "Dual Antimicrobial Silicone Adhesive Dressings. A White Paper. What's the Difference, and Why It Matters.," www.covalon.com; Covalon Technologies Ltd. (2013).
Groesbeck, Michael L., "Cardinal Health Letter to Food and Drug Administration Re ANDA for Preoperative Prep with Tint," (Nov. 18, 2004).
Hamilton, Chris, "ChloraPrep Pros & Cons," http://www.ehow.com/list_6884562_chloraprep-pros-_amp_amp_-cons.html (Nov. 9, 2011).
Hemani, Micah L. et al., "Skin Preparation for the Prevention of Surgical Site Infection: Which Agent is Best?", *Reviews in Urology*, vol. 11, No. 4 (2009) pp. 190-195.
Joseph, Siji, "Quantification of 4-Chloroaniline in Chlorhexidine Using the Agilent 1200 Series Rapid Resolution LC System Coupled with the Agilent 6410B Triple Quadrupole LC/MS System," Agilent Technologies, Inc., Publication No. 5990-3676EN (Mar. 15, 2009).
Karpanen, TJ et al., "Penetration of Chlorhexidine into Human Skin," *Antimicrob Agents Chemother.*, Oct. 2008;52(10):3633-6.
Kohlbecker, G., "Toxic Impurities in Chlorhexidine Digluconate," *Deutsche Zahnarztliche Zeitschrift*, 44(4):273-276, (1989) [Abstract].
Moureau, Nancy L., et al., "Evaluation of the Clinical Performance of a Chlorhexidine Gluconate Antimicrobial Transparent Dressing," *Journal of Infection Prevention*, 2009; vol. 10,. Supp. 1 http://bji.sagepub.com/cgi/content/abstract/10/1_suppl/s13, (Sep. 30, 2009).
Nicolay, Alain et al., "Rapid HPLC Method for Determination of Parachloroaniline in Chlorhexidine Antiseptic Agent in Mouthrinses, Ophthalmic and Skin Solution," *American Journal of Analytical Chemistry*, vol. 2 (Aug. 31, 2011) pp. 422-428.
Ranganathan, N. S., "Chlorhexidine," *Handbook of Antiseptics and Disinfectants*, Marcel Dekker, Inc. (New York), Joseph Ascenzi (ed.) (1996) pp. 236-237.
Tallury, Padmavathy et al., "Poly(ethylene-co-vinyl acetate) Copolymer Matrix for Delivery of Chlorhexidine and Acyclovir Drugs for Use in the Oral Environment: Effect of Drug Combination, Copolymer Composition and Coating on the Drug Release Rate," *Dent Mater.*, 23(4):404-9. (Apr. 2007) [Epub Mar. 23, 2006].
Ward, J. H., et al., "Micropatterning of Biomedical Polymer Surfaces by Novel UV Polymerization Techniques," *J. Biomed. Mater. Res.*, 56:351-360 (Apr. 24, 2001).
Zong, Zhixin et al., "Studies on the Instability of Chlorhexidine, Part I: Kinetics and Mechanisms," *Journal of Pharmaceutical Sciences*, vol. 101, No. 7 (Jul. 2012) pp. 2417-2427.
"Hyperbranched Urethane-Acrylates," *European Coatings Journal*, Issue Jun. 2004, p. 36.
"Urethane Acrylate Oligomers," *Sartomer* [retrieved on Jan. 2, 2020 from https://emea.sartomer.com/en/products/specialty-acrylates-resins/urethane-acrylates/].

* cited by examiner

METHODS OF PROCESSING CHLORHEXIDINE-CONTAINING POLYMERIZABLE COMPOSITIONS AND ANTIMICROBIAL ARTICLES FORMED THEREBY

BACKGROUND OF THE INVENTION

The present invention relates generally to methods of processing chlorhexidine-containing polymerizable compositions and antimicrobial articles formed thereby.

The United States' Center for Disease Control (CDC) recommends chlorhexidine gluconate as the preferred skin antiseptic over tinctures of iodine, iodophors, and alcohol. Chlorhexidine, a substituted diguanide, has a high degree of antimicrobial activity, low mammalian toxicity, and the ability to bind to the stratum corneum layer of skin and to mucous membranes. The bactericidal activity of chlorhexidine is much greater than that of monomeric biguanides. These unique characteristics make it particularly attractive as an active ingredient in antimicrobial skin preparations. Besides its use in specific medical dressings and skin antiseptics, the efficacy of chlorhexidine in providing antimicrobial protection is known further throughout the medical industry. However, when incorporated into polymerizable compositions, elevated processing temperatures are often used, which can potentially damage the chlorhexidine within.

An example of such elevated temperature processing is described in U.S. Pat. No. 5,165,952, where a temperature range of 160° C.-250° C. is used. Referencing the same, U.S. Pat. No. 8,383,143 states: "When chlorhexidine is bulk distributed it adversely affects certain characteristics of the device such as tensile strength, and the high temperatures needed for extension of plastics such as polyurethane may damage the chlorhexidine." U.S. Patent Publication No. 2013/0303656 similarly references the negative effects associated with processing chlorhexidine-containing materials at elevated temperatures.

Not only does processing at elevated temperatures potentially decrease efficacy of chlorhexidine-containing articles, but it is also known to create a toxic chemical. Hydrolysis of chlorhexidine yields p-chloroaniline (also referred to as 4-chloroaniline, but referred to hereinafter as PCA). The amount of PCA generated is relatively insignificant at room temperature, but becomes more significant as temperature is increased by heating, especially at alkaline pH. At temperatures of about 40° C. or greater, chlorhexidine is documented as decomposing to PCA, as described in, for example, Ranganathan, N. S. (1996), "Chlorhexidine," in Ascenzi, Joseph M. (Ed.), *Handbook of Antiseptics and Disinfectants*, Marcel Dekker, Inc. (New York), pp. 235-265. Thus, when thermal processing of chlorhexidine-containing articles is employed, introduction of PCA therein has been unavoidable.

Many polymer-based materials are processed at elevated temperatures. For example, see U.S. Patent Publication No. 2011/313048, which describes an antimicrobial silicone-based wound dressing formed from a liquid containing silicone and employing particulates of a chlorhexidine compound that is not soluble in the liquid, where processing temperatures of 100° C.-150° C. are described. In general, continuous web-based processing of polymerizable compositions often occurs at temperatures of 80° C.-100° C. Thus, decomposition of chlorhexidine incorporated therein to PCA is not only prevalent along the length of a moving web when subjected to such continuous processing, but it becomes even more so at locations along the web that were halted during processing, which often occurs and often involves excess exposure time to heating elements positioned along the web.

In view of the toxic nature of PCA, desired are new methods of processing chlorhexidine-containing polymerizable compositions and antimicrobial articles formed thereby, wherein PCA formation is minimized.

BRIEF SUMMARY OF THE INVENTION

A method of forming an antimicrobial article according to the invention comprises steps of: providing a polymerizable composition; incorporating an antimicrobially effective amount of at least one chlorhexidine-containing antimicrobial agent into the polymerizable composition; and, polymerizing the polymerizable composition to form chlorhexidine-containing polymer of the antimicrobial article, wherein processing temperature during the method is less than about 80° C. In a further embodiment, the processing temperature during the method is less than about 40° C., preferably less than about 35° C. or, more preferably, less than about 30° C. In a still further embodiment, the processing temperature during the method is about room temperature (i.e., 22° C.-25° C.). Preferably, to maximize benefits of the invention, the processing temperature during the method is less than that temperature at which chlorhexidine decomposes to PCA.

The antimicrobially effective amount of at least one chlorhexidine-containing antimicrobial agent in the antimicrobial article consists essentially of chlorhexidine free base in one embodiment. For example, in one embodiment, an antimicrobial article prepared according to the method of the invention comprises about 10 weight % chlorhexidine free base based on total weight of the chlorhexidine-containing polymer. In another embodiment, the antimicrobially effective amount of at least one chlorhexidine-containing antimicrobial agent comprises chlorhexidine salt.

An exemplary method comprises continuously forming the chlorhexidine-containing polymer on a web. According to one aspect of the invention, polymerization of the polymerizable composition is initiated using at least one radiation source selected from ultraviolet radiation and electron beam radiation. According to another aspect of the invention, polymerization of the polymerizable composition is initiated without use of an external source of thermal radiation. For example, 100% reactive chemistry is used to form the chlorhexidine-containing polymer in one embodiment.

Preferably, the polymerizable composition formed according to methods of the invention is essentially free of solvents. In one embodiment, the chlorhexidine-containing polymer is essentially free of unreacted solvent.

While it may take many forms, in one embodiment, the chlorhexidine-containing polymer is a polymer film. According to one aspect of the invention, the chlorhexidine-containing polymer is an adhesive. According to another aspect of the invention, the chlorhexidine-containing polymer is a backing for an adhesive-coated antimicrobial article.

The chlorhexidine-containing polymer may also comprise any suitable chemistry. In one embodiment, the chlorhexidine-containing polymer comprises at least one base polymer selected from polycarbonates, polyvinyl fluorides, poly (meth)acrylates, polyurethanes, and modified polymers thereof. An exemplary chlorhexidine-containing polymer is polyurethane-based. Another exemplary chlorhexidine-containing polymer is (meth)acrylate-based.

Advantageously, PCA is minimal in antimicrobial articles prepared according to the method of the invention. In one embodiment, an antimicrobial article prepared according to the method of the invention has less than about 0.0001 mg/mL detectable PCA present in the chlorhexidine-containing polymer. In a further embodiment, an antimicrobial article prepared according to the method of the invention has essentially no detectable PCA present in the chlorhexidine-containing polymer.

DETAILED DESCRIPTION OF THE INVENTION

Antimicrobial articles of the invention are chlorhexidine-containing. Chlorhexidine-containing antimicrobial articles comprise an antimicrobially effective amount of chlorhexidine in its pure form (i.e., as a free base), an antimicrobially effective amount of chlorhexidine in the form of at least one chlorhexidine salt, or combinations thereof. Unlike widespread use of the general term chlorhexidine by those of ordinary skill in the art in referring only to the salt form of chlorhexidine, unless specifically stated herein, reference to the general term chlorhexidine in describing the invention herein is meant to include both the pure form and salt form of chlorhexidine.

In one embodiment, chlorhexidine-containing antimicrobial articles comprise at least one chlorhexidine salt. Suitable counterions for chlorhexidine in salts thereof include, but are not limited to, dihydrochloride, methosulfate, diphosphanilate, palmitate, lactate, gluconate, diacetate, and the like. An exemplary chlorhexidine salt is chlorhexidine gluconate (CHG), which is sometimes referred to by those of ordinary skill in the art as chlorhexidine digluconate.

In another embodiment, chlorhexidine is present in its substantially pure form (i.e., as a free base). When using pure chlorhexidine, antimicrobial activity is typically increased as compared to use of chlorhexidine salts. It is believed that lack of bonding between chlorhexidine and the polymeric composition in which it is dispersed (as compared to the at least ionic bonding present when chlorhexidine salts are dispersed in a polymeric composition) contributes to improved release of chlorhexidine from the polymeric composition and, hence, antimicrobial effect.

Antimicrobial articles of the invention comprise any suitable polymeric materials (also referred to herein simply as "polymers"), which can be formed into a wide variety of shapes suitable for their intended application. Some applications impose more stringent requirements on dimensions or other properties of materials used than others. For example, optical clarity of polymeric materials is an important consideration when selecting polymeric materials for use in optical applications. As a further example, many applications require that polymeric materials used therein consist of single layer films having controlled dimensions.

A "film" is generally understood to be a relatively thin, continuous, single layer of solid material. In contrast, many conventionally applied "coatings" do not form a continuous or uniform layer of material on an underlying substrate. As such, once excess solvent (i.e., organic solvent and/or water) is dried, liquid-applied coatings (e.g., vapor coatings and ink jet-printed coatings) are often not able to be physically separated from the supporting substrate on which they are formed so that they can be used as a stand-alone layer or as one of multiple layers in another application. Thus, such coating technology has its limitations and is generally deficient for formation of polymeric films.

In exemplary embodiments, polymer films formed according to methods of the invention are able to be physically separated from the supporting substrate on which they are formed so that they can be used as a stand-alone layer or as one of multiple layers in antimicrobial articles. Recognize, however, that polymer films may be formed contiguously with or subsequently laminated to other polymer films or layers (e.g., adhesive layers or release liners) according to further embodiments.

Antimicrobial articles and chlorhexidine-containing polymerizable compositions used to form the same according to methods of the invention comprise any suitable material. Chemistry of materials used herein is not limited so long as processing temperatures associated therewith fall within those of the present invention. Suitable chemistries may comprise polyolefins (e.g., low density polyethylene), polyurethanes (e.g., polyester polyurethane or polyether polyurethane), polyesters (e.g., polyether polyester), and polyamides (e.g., polyether polyamide). In an exemplary embodiment, antimicrobial articles of the invention comprise at least one base polymer selected from polycarbonates, polyvinyl fluorides, poly(meth)acrylates (e.g., a polyacrylate or a polymethacrylate), polyurethanes, and modified polymers thereof (e.g., a hybrid).

By use of the term "polymerizable," it is to be understood that such a composition contains components that will polymerize upon initiation using any suitable method. The polymerizable composition may exist in one or multiple parts, depending on the nature of the components therein. It is also to be understood that each part of the polymerizable composition may itself comprise more than one premixed components.

"Polymerizable compositions" of the invention include at least two different components (e.g., monomers, which can be mono-, di-, tri-functional, etc.), wherein the two components are mutually reactive with each other via chemically different reactive moieties to form a polymeric backbone. The two components may react to form the polymeric backbone in linear, branched, and/or networked polymers. In preferred embodiments, polymerizable compositions are polymerizable using free radical growth or similar polymerization methods capable of being initiated using a radiation source. For example, poly(meth)acrylates, polyurethanes, polyureas, and polyvinyls are capable of being formed according to the invention using such polymerization methods.

Understand that a polymerizable composition may be partially polymerized or essentially non-polymerized. In an exemplary embodiment, each of the at least two different components forming the polymerizable composition has an average molecular weight that is less than about 1% of the weight average molecular weight of the fully polymerized composition. In another exemplary embodiment, each of the at least two different components forming the polymerizable composition has an average molecular weight that is less than about 10% of the weight average molecular weight of the fully polymerized composition. In yet another exemplary embodiment, each of the at least two different components forming the polymerizable composition has an average molecular weight that is less than about 50% of the weight average molecular weight of the fully polymerized composition.

Exemplary polymers in antimicrobial articles formed according to methods of the invention are polyurethane-based. For simplicity, the term "polyurethane" as used herein includes polymers containing urethane (also known as carbamate) linkages, urea linkages, or combinations thereof (i.e., in the case of poly(urethane-urea)s). Thus, polyurethane-based compositions contain at least urethane linkages, urea linkages, or combinations thereof. Furthermore, polyurethane-based polymers are based on polymers where the polymeric backbone has at least 80% urethane and/or urea repeat linkages formed during the polymerization process.

Polyurethane-based polymers are prepared according to methods of the invention by reacting components, which include at least one isocyanate-reactive (e.g., hydroxy-functional, such as polyol) component and at least one isocyanate-functional (e.g., polyisocyanate) component. For example, components of exemplary polymerizable compositions and which are useful in the formation of polyurethane-based polymers according to methods of the invention are described in U.S. Patent Publication No. US-2011-0241261-A1, entitled "Methods for Polymerizing Films In-Situ Using a Radiation Source" and incorporated herein by reference in its entirety.

In order to minimize decomposition of chlorhexidine to PCA within polymerizable compositions during processing thereof to form antimicrobial articles, antimicrobial articles of the invention are formed using relatively low temperature processing—i.e., processing at temperatures less than 80° C., preferably at temperatures less than about 60° C., more preferably at temperatures less than about 40° C., even more preferably less than about 35° C., and even more preferably less than about 30° C. In an exemplary embodiment, processing occurs at about room temperature—i.e., about 22° C.-25° C. If elevated temperatures are used at any time during processing, their duration is minimized. Preferably, however, temperatures used during processing never, even briefly, exceed 80° C. or, when used, the preferred lower temperature limits.

In exemplary embodiments, the polymerization of the polymerizable composition is initiated using at least one radiation source selected from ultraviolet radiation, thermal radiation, and electron beam radiation. In one embodiment, polymerization of the polymerizable composition is initiated without use of an external source of thermal radiation. If needed, at least one of ultraviolet radiation and electron beam radiation is used in one embodiment of the invention in order to initiate polymerization of chlorhexidine-containing polymerizable compositions when making chlorhexidine-containing antimicrobial articles of the invention. Preferably, use of thermal radiation is minimized or eliminated during all processing of materials comprising chlorhexidine when forming antimicrobial articles according to methods of the invention.

Methods of the invention can utilize continuous processing or batch processing. For example, continuous processing, such as web-based polymerization using relatively low energy ultraviolet radiation, can be used in one embodiment of the invention. As another example, batch processing, such as coating ultraviolet-curable composition on a discrete substrate and irradiating the same, can be used in another embodiment of the invention.

A wide variety of antimicrobial articles can be formed according to the present invention. In an exemplary embodiment, an antimicrobial article comprises an adhesive-coated backing—e.g., an adhesive laminated to, or coated on, a backing. In this embodiment, at least one of the backing and the adhesive contains chlorhexidine.

An exemplary embodiment of forming such a backing comprises 100% reactive chemistry, such as urethane-based chemistry, where no or minimal radiation (e.g., thermal, electron beam, or ultraviolet radiation) is used to form the backing, which can be a continuous web-based process or batch process.

An exemplary embodiment of forming such an adhesive comprises 100% reactive chemistry, such as (meth)acrylate-based chemistry, where no or minimal radiation (e.g., thermal, electron beam, or ultraviolet radiation) is used to form the adhesive, which can be a continuous web-based process or a batch process.

Another exemplary method of forming such an adhesive comprises using ultraviolet radiation. For example, a polymerizable adhesive composition comprising a thixotrope and ultraviolet polymerization initiator can be roll-coated onto a substrate and then subjected to ultraviolet radiation to polymerize the composition to an adhesive. U.S. Patent Publication No. US-2011-0241261-A1 describes such a useful polymerization method for the present invention. U.S. Patent Publication No. US-2011-0137006-A1, entitled "Methods for Polymerizing Films In-Situ" and incorporated herein by reference in its entirety, describes another useful polymerization method for the present invention.

According to a preferred aspect of methods of the invention, the chlorhexidine-containing polymerizable composition is essentially free of solvents. In addition to, for example, environmental and safety concerns associated with solvent-based processing, solvent-based processing typically entails use of elevated temperatures for effective removal of excess solvent from the polymerized composition. It is preferred that polymers in antimicrobial articles formed according to methods of the invention are essentially free of unreacted solvent. Thus, it is preferred that the polymerizable compositions from which they are formed are essentially free of solvents.

The amount of PCA within an antimicrobial article formed according to methods of the invention can be quantitatively analyzed using any suitable analytical methodology. PCA's observed limit of detection (LOD) is 0.2 ng/mL and the limit of quantification (LOQ) is 0.3 ng/mL according to Agilent Technologies ("Analytical Methodology for PCA Detection: Quantification of 4-Chloroaniline in Chlorhexidine Using the Agilent 1200 Series Rapid Resolution LC System Coupled with the Agilent 6410B Triple Quadrupole LC/MS System," Agilent Technologies, Inc., Mar. 15, 2009, Publication Number 5990-3676EN). According to the analytical method described therein, PCA present in a sample reacts with nitrous acid and $\alpha$-naphthol to give a measurable red-colored derivative.

Exemplary embodiments and applications of the invention are described in the following non-limiting examples.

EXAMPLES

Film Formation Method

Into a mixing tank with agitating blades operating at 60 Hertz, an adhesive precursor, commercially available from entrochem, inc. (Columbus, Ohio) under the trade designation, 320650, was pumped using a diaphragm pump. To the adhesive precursor and via a port in the top of the mixing tank, chlorhexidine was added in powder form to the desired total weight percentage at a rate of from 1 to 50,000 grams/hour. During addition of the chlorhexidine, the contents of the mixing tank were recirculated from bottom to top, passing through a static mixer along the way. Upon addition of chlorhexidine to the desired amount, a degas/mix cycle was run for one hour and pulling a vacuum on the mixing tank to a minimum of about 66 kPa absolute pressure (i.e., about 10 inches of mercury below atmospheric pressure), after which time period the contents of the mixing tank were immediately dispensed for coating. The contents were coated on-web at a coating line speed of 38 m/min (125 ft/min) under ultraviolet lights operating at a wavelength of 350-400 nm (typically peaking at 369 nm) and having an irradiance of 20 mW/cm$^2$. Temperature during all of the above processing steps was maintained at room temperature.

Extraction and Assay Method for Film

A 10-cm- by 10-cm-square sample of the film was placed in a glass vial, which was certified to meet or exceed EPA standards for volatiles. To the vial, 15 mL of tetrahydrofuran (THF) was added. The vial was then placed on a wrist-action shaker for at least sixteen hours. Then, 5 mL of the vial contents was diluted to a volume of 10 mL with a solution of 27.6 grams monobasic sodium phosphate (0.36 weight % monobasic sodium phosphate based on total weight of the diluent such that its molarity was 0.115 mol/L), 10 milliliters triethylamine (1.36 weight % triethylamine based on total weight of the diluent such that its molarity was 0.036 mol/L), and 10 milliliters water (98.28 weight % water based on total weight of the diluent), with the diluent adjusted with phosphoric acid to a pH of 3.0. The resulting solution was vortexed for about fifteen seconds, after which time an aliquot thereof was filtered through a 0.45 μm pore size nylon filter membrane within a syringe-tip. The resulting filtrate was then analyzed for PCA analyte using high performance liquid chromatographic (HPLC) analysis according to U.S. Pharmacopeial Convention standards for analysis of chlorhexidine hydrochloride in a HPLC system using an LC mode and 239-nanometer ultraviolet detector. A 4.6-mm×25-cm column was used with a base-deactivated 5-μm USP Code L1 packing (i.e., octadecyl silane chemically bonded to porous silica or ceramic micro-particles as known to those of ordinary skill in the art). The column temperature was maintained at 40° C. and the flow rate was maintained within the column at the rate of 1.5 mL/min using a 50 μL injection size.

Example 1

An adhesive film prepared according to the Film Formation Method and containing 2 weight % chlorhexidine based on total weight of the adhesive was evaluated according to the Extraction and Assay Method for Film described above. The evaluation was repeated for a total of 12 samples of the same film. No PCA was detected.

Example 2

A sterilized adhesive film prepared according to the Film Formation Method and containing 2 weight % chlorhexidine based on total weight of the adhesive was evaluated according to the Extraction and Assay Method for Film described above. The evaluation was repeated for a total of 12 samples of the same film. Each sample was sterilized to a dose of 25 kGy gamma radiation. No PCA was detected.

Example 3

A sterilized adhesive film prepared according to the Film Formation Method and containing 2 weight % chlorhexidine based on total weight of the adhesive was evaluated according to the Extraction and Assay Method for Film described above. The evaluation was repeated for a total of 12 samples of the same film. Each sample was sterilized to a dose of 25 kGy gamma radiation and aged at an accelerated rate for six months according to ASTM Test Method F1980. No PCA was detected.

Example 4

A sterilized adhesive film prepared according to the Film Formation Method and containing 2 weight % chlorhexidine based on total weight of the adhesive was evaluated according to the Extraction and Assay Method for Film described above. The evaluation was repeated for a total of 12 samples of the same film. Each sample was sterilized to a dose of 25 kGy gamma radiation and aged at an accelerated rate for twenty-four months according to ASTM Test Method F1980. No PCA was detected.

Example 5

An adhesive film prepared according to the Film Formation Method and containing 2 weight % chlorhexidine based on total weight of the adhesive was evaluated according to the Extraction and Assay Method for Film described above. The evaluation was repeated for a total of 10 samples of the same film. No PCA was detected.

Example 6

A sterilized adhesive film prepared according to the Film Formation Method and containing 2 weight % chlorhexidine based on total weight of the adhesive was evaluated according to the Extraction and Assay Method for Film described above. The evaluation was repeated for a total of 12 samples of the same film. Each sample was sterilized to a dose of 42 kGy gamma radiation. No PCA was detected.

Example 7

A sterilized adhesive film prepared according to the Film Formation Method and containing 2 weight % chlorhexidine based on total weight of the adhesive was evaluated according to the Extraction and Assay Method for Film described above. The evaluation was repeated for a total of 12 samples of the same film. Each sample was sterilized to a dose of 42 kGy gamma radiation. No PCA was detected.

Example 8

A sterilized adhesive film prepared according to the Film Formation Method and containing 2 weight % chlorhexidine based on total weight of the adhesive was evaluated according to the Extraction and Assay Method for Film described above. The evaluation was repeated for a total of 12 samples of the same film. Each sample was sterilized to a dose of 42 kGy gamma radiation and aged in real time for two months. No PCA was detected.

Example 9

An adhesive film prepared according to the Film Formation Method and containing 10 weight % chlorhexidine based on total weight of the adhesive was evaluated according to the Extraction and Assay Method for Film described above. The evaluation was repeated for a total of 8 samples of the same film. No PCA was detected.

Example 10

A sterilized adhesive film prepared according to the Film Formation Method and containing 10 weight % chlorhexidine based on total weight of the adhesive was evaluated according to the Extraction and Assay Method for Film described above. The evaluation was repeated for a total of 12 samples of the same film. Each sample was sterilized to a dose of 43 kGy gamma radiation. No PCA was detected.

Example 11

An adhesive film prepared according to the Film Formation Method and containing 10 weight % chlorhexidine based on total weight of the adhesive was evaluated according to the Extraction and Assay Method for Film described above. The evaluation was repeated for a total of 12 samples of the same film. No PCA was detected.

Example 12

A sterilized adhesive film prepared according to the Film Formation Method and containing 10 weight % chlorhexidine based on total weight of the adhesive was evaluated according to the Extraction and Assay Method for Film described above. The evaluation was repeated for a total of 12 samples of the same film. Each sample was sterilized to a dose of 43 kGy gamma radiation and aged at an accelerated rate for twelve months according to ASTM Test Method F1980. No PCA was detected.

Comparative Example C1

Wound dressing film containing chlorhexidine and commercially sold by Covalon Technologies Ltd. of Mississauga, Ontario, Canada as SURGICLEAR Antimicrobial Clear Silicone Surgical Dressing was evaluated about six months before its expiration date according to the Extraction and Assay Method for Film described above. The evaluation was repeated for a total of 4 samples of the same film. PCA in the amount of 0.0001 mg/mL was detected in each of the samples.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

Further, as used throughout, ranges may be used as shorthand for describing each and every value that is within the range. Any value within the range can be selected as the terminus of the range. Similarly, any discrete value within the range can be selected as the minimum or maximum value recited in describing and claiming features of the invention.

In addition, as discussed herein it is again noted that compositions described herein may comprise all components in one or multiple parts. Further, while reference may be made herein to preparation of the various intermediate components, recognize that some such intermediate components may be commercially available and, as such, can be used according to the invention as an alternative to otherwise preparing the same. Other variations are recognizable to those of ordinary skill in the art.

The invention claimed is:

1. A method of forming an antimicrobial article, the method comprising steps of:
   providing a polymerizable composition comprising at least two different components, wherein each of the at least two different components are mutually reactive with each other via chemically different reactive moieties to form a polymeric backbone, and wherein each of the at least two different components has an average molecular weight that is less than about 50% of the weight average molecular weight of the fully polymerized composition;
   incorporating an antimicrobially effective amount of at least one chlorhexidine-containing antimicrobial agent into the polymerizable composition; and,
   polymerizing the polymerizable composition to form chlorhexidine-containing polymer of the antimicrobial article,
wherein processing temperature during the method is less than about 40° C., and,
wherein the method comprises continuously forming the chlorhexidine-containing polymer on a web.

2. The method of claim 1, wherein the processing temperature during the method is about room temperature.

3. The method of claim 1, wherein the processing temperature during the method is less than that temperature at which chlorhexidine decomposes to para-chloroaniline.

4. The method of claim 1, wherein the antimicrobially effective amount of at least one chlorhexidine-containing antimicrobial agent in the antimicrobial article consists essentially of chlorhexidine free base.

5. The method of claim 1, wherein the antimicrobially effective amount of at least one chlorhexidine-containing antimicrobial agent comprises chlorhexidine salt.

6. A method of forming an antimicrobial article, the method comprising steps of:
   providing a polymerizable composition comprising at least two different components, wherein each of the at least two different components are mutually reactive with each other via chemically different reactive moieties to form a polymeric backbone, and wherein each of the at least two different components has an average molecular weight that is less than about 50% of the weight average molecular weight of the fully polymerized composition;
   incorporating an antimicrobially effective amount of at least one chlorhexidine-containing antimicrobial agent into the polymerizable composition; and,
   polymerizing the polymerizable composition to form chlorhexidine-containing polymer of the antimicrobial article,
wherein processing temperature during the method is less than about 40° C., and,
wherein the polymerizable composition is essentially free of solvents.

7. A method of forming an antimicrobial article, the method comprising steps of:
   providing a polymerizable composition comprising at least two different components, wherein each of the at least two different components are mutually reactive with each other via chemically different reactive moieties to form a polymeric backbone, and wherein each of the at least two different components has an average molecular weight that is less than about 50% of the weight average molecular weight of the fully polymerized composition;

incorporating an antimicrobially effective amount of at least one chlorhexidine-containing antimicrobial agent into the polymerizable composition; and, polymerizing the polymerizable composition to form chlorhexidine-containing polymer of the antimicrobial article, wherein processing temperature during the method is less than about 40° C., and, wherein the chlorhexidine-containing polymer is essentially free of unreacted solvent.

8. The method of claim 1, wherein polymerization of the polymerizable composition is initiated using at least one radiation source selected from ultraviolet radiation and electron beam radiation.

9. The method of claim 1, wherein polymerization of the polymerizable composition is initiated without use of an external source of thermal radiation.

10. The method of claim 1, wherein the chlorhexidine-containing polymer is a polymer film.

11. The method of claim 1, wherein the chlorhexidine-containing polymer is an adhesive.

12. The method of claim 1, wherein the chlorhexidine-containing polymer is a backing for an adhesive-coated antimicrobial article.

13. The method of claim 1, wherein 100% reactive chemistry is used to form the chlorhexidine-containing polymer.

14. The method of claim 1, wherein the chlorhexidine-containing polymer comprises at least one base polymer selected from polycarbonates, polyvinyl fluorides, poly(meth)acrylates, polyurethanes, and modified polymers thereof.

15. The method of claim 1, wherein the chlorhexidine-containing polymer is (meth)acrylate-based.

16. A method of forming an antimicrobial article, the method comprising steps of:

providing a polymerizable composition comprising at least two different components, wherein each of the at least two different components are mutually reactive with each other via chemically different reactive moieties to form a polymeric backbone, and wherein each of the at least two different components has an average molecular weight that is less than about 50% of the weight average molecular weight of the fully polymerized composition;

incorporating an antimicrobially effective amount of at least one chlorhexidine-containing antimicrobial agent into the polymerizable composition; and, polymerizing the polymerizable composition to form chlorhexidine-containing polymer of the antimicrobial article, wherein processing temperature during the method is less than about 40° C., and, wherein the at least one chlorhexidine-containing antimicrobial agent is in powder form.

17. A method of forming an antimicrobial article, the method comprising steps of:

providing a polymerizable composition comprising at least two different components, wherein each of the at least two different components are mutually reactive with each other via chemically different reactive moieties to form a polymeric backbone, and wherein each of the at least two different components has an average molecular weight that is less than about 50% of the weight average molecular weight of the fully polymerized composition;

incorporating an antimicrobially effective amount of at least one chlorhexidine-containing antimicrobial agent into the polymerizable composition; and, polymerizing the polymerizable composition to form chlorhexidine-containing polymer of the antimicrobial article, wherein processing temperature during the method is less than about 40° C., and, wherein the polymerizable composition is essentially non-polymerized.

18. A method of forming an antimicrobial article, the method comprising steps of:

providing a polymerizable composition comprising at least two different components, wherein each of the at least two different components are mutually reactive with each other via chemically different reactive moieties to form a polymeric backbone, and wherein each of the at least two different components has an average molecular weight that is less than about 50% of the weight average molecular weight of the fully polymerized composition;

incorporating an antimicrobially effective amount of at least one chlorhexidine-containing antimicrobial agent into the polymerizable composition; and, polymerizing the polymerizable composition to form chlorhexidine-containing polymer of the antimicrobial article, wherein processing temperature during the method is less than about 40° C., and, wherein each of the at least two different components has an average molecular weight that is less than about 1% of the weight average molecular weight of the fully polymerized composition.

19. The method of claim 1, wherein the chlorhexidine-containing polymer is polyurethane-based.

20. The method of claim 1, wherein the chlorhexidine-containing polymer is (meth)acrylate-based.

21. A method of forming an antimicrobial article, the method comprising steps of:

providing a polymerizable composition comprising at least two different components, wherein each of the at least two different components are mutually reactive with each other via chemically different reactive moieties to form a polymeric backbone, and wherein each of the at least two different components has an average molecular weight that is less than about 50% of the weight average molecular weight of the fully polymerized composition;

incorporating an antimicrobially effective amount of at least one chlorhexidine-containing antimicrobial agent into the polymerizable composition; and, polymerizing the polymerizable composition to form chlorhexidine-containing polymer of the antimicrobial article, wherein processing temperature during the method is less than about 40° C., and, wherein each of the at least two different components has an average molecular weight that is less than about 10% of the weight average molecular weight of the fully polymerized composition.

* * * * *